United States Patent [19]

Daluge

[11] Patent Number: 5,039,689
[45] Date of Patent: Aug. 13, 1991

[54] ANTIPARASITIC 3(4-AMINO BENZOTRIAZO-1-YL-)1,2-CYCLOPENTANEDIOLS

[75] Inventor: Susan M. Daluge, Chapel Hill, N.C.

[73] Assignee: Burroughs Wellcome Co., Triangle Park, N.C.

[21] Appl. No.: 433,484

[22] Filed: Nov. 8, 1989

[30] Foreign Application Priority Data

Nov. 9, 1988 [GB] United Kingdom ............ 8826205.0

[51] Int. Cl.$^5$ .................... C07D 249/18; A01N 43/64
[52] U.S. Cl. .................... 514/359; 514/248; 514/300; 514/303; 514/394; 544/254; 546/117; 546/118; 548/260; 548/326
[58] Field of Search .................... 514/359; 548/260

[56] References Cited

U.S. PATENT DOCUMENTS

| | | | |
|---|---|---|---|
| 3,004,896 | 10/1961 | Heller et al. | 514/359 |
| 3,808,334 | 4/1974 | Dahle | 514/359 |
| 4,038,403 | 7/1977 | Wright | 514/359 |
| 4,086,242 | 4/1978 | Diehl et al. | 71/92 |
| 4,755,215 | 7/1988 | Haga | 548/260 |
| 4,859,677 | 8/1989 | Borchardt et al. | 544/271 |

FOREIGN PATENT DOCUMENTS 1198995 10/1959 France .................... 514/359

OTHER PUBLICATIONS

E. L. Pesanti, The Journal of Infectious Diseases, vol. 141, No. 6, Jun. 1980, pp. 775-780, In Vitro Effects of Antiprotozoan Drugs and Immune Serum on Pneumocystis Carinii.

Cermak et al., Tetrahedron Letters, vol. 22, No. 25, 1981, pp. 2331-2332, (+), 4β-Amino-2α,3-Dihydroxy-1β-Cyclopentanemethanol Hydrochloride. Carbocyclic Ribofuranosylamine for the Synthesis of Carbocyclic Nucleosides.

Vince et al., Journal of Medicinal Chemistry, vol. 17, No. 6, 1974, pp. 578-583, Puromycin Analogs. 1 Studies on Ribosomal Binding with Diastereomeric Carbocyclic Puromycin Analogs.

Shealy et al., Journal of the American Chemical Society, 91:11, May 21, 1969, pp. 3075-3083, Synthesis of Carbocyclic Analogs of Purine Ribonucleosides[1].

Daluge et al., J. Org. Chem., vol. 43, No. 12, 1978, pp. 2311-2320, Synthesis of Carbocyclic Aminonucleosides.

Montgomery et al., Nucleoside Analogs as Antiviral Agents, pp. 409-417.

Houston et al., J. Med. Chem., 1985, 28, pp. 478-482, Potential Inhibitors of S-Adenosylmethionine-Dependent Methyltransferases. 10, Base- and Amino Acid Modified Analogues of S-Aristeromycinyl-L-Homocysteinela.

Hayashi et al., The Journal of Antibiotics, vol. XXXIV, No. 6, Jun. 1981, pp. 675-680, Studies on Neplanocin A, New Antitumor Antibiotic. II, Structure Determination.

Primary Examiner—Donald G. Daus
Attorney, Agent, or Firm—Donald Brown

[57] ABSTRACT

The present invention relates to the use of a compound of formula (I)

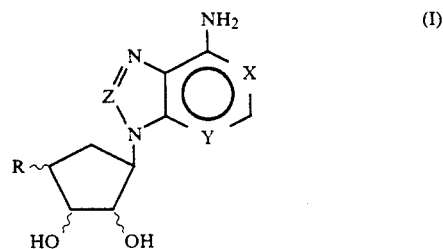

wherein
R represents
  a hydrogen atom; a $C_{1-4}$ alkyl group;
  a group $COR^1$ wherein $R^1$ represents amino or $C_{1-4}$ alkoxy; or
  a group $—CH_2R^2$ wherein $R^2$ represents a halogen atom (e.g. chlorine or bromine), $C_{1-4}$ alkylthio, or azido,
X and Y each independently represent —CH— or —N; and
Z represents $—CR^3$, wherein $R^3$ is hydrogen or $C_{1-4}$ alkyl, or Z represents —N—;
or a physiologically acceptable salt, ester or other physiologically functional derivative thereof, for the manufacture of a medicament for the treatment and/or prophylaxis of a parasitic infection in a mammal, and to certain novel compounds of formula (I), pharmaceutical compositions containing them and processes for their preparation.

8 Claims, No Drawings

ANTIPARASITIC 3(4-AMINO BENZOTRIAZO-1-YL-)1,2-CYCLOPENTANEDIOLS

The present invention relates to novel carbocyclic nucleoside derivatives, pharmaceutical compositions containing them, processes for their preparation and their use in medicine in particular for the treatment of parasitic infections. The present invention also relates to the use of certain known carbocyclic nucleoside derivatives in treating said infections.

EPA 267878 discloses compounds of the formula:

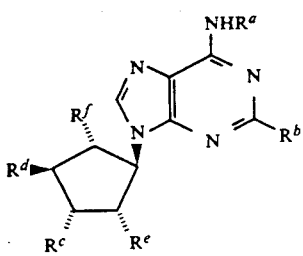

where $R^a$, $R^b$ and $R^f$ each represent inter alia hydrogen, $R^c$ and $R^e$ each represent inter alia hydroxy and $R^d$ represents inter alia lower alkylthiomethyl or —CONHR$^g$ where R$^g$ is inter alia lower alkyl. These compounds are said to be adenosine receptor agonists which may be useful in treating e.g. cardiovascular conditions and central nervous system conditions.

Hayashi and Yaginuma (J. Antibiotics XXXIV, No. 6, p675-680) describe a number of derivatives prepared in the course of the structural elucidation of neplanocin A, including a cyclopentane derivative of the above formula wherein $R^a$, $R^b$ and $R^f$ are each hydrogen, $R^c$ and $R^e$ are each hydroxy and $R^d$ is methyl (no stereochemistry is assigned). No biological activity is ascribed to this compound.

The compound of the above formula wherein $R^a$, $R^b$ and $R^f$ are each hydrogen, $R^c$ and $R^e$ each hydroxyl and $R^d$ is chloromethyl and the corresponding 7-amino-1,2,3-triazolo[4,5-d]pyrimidine compound are described by Houston et al (J. Med. Chem, 1985, 28(4), 478-82) as potential inhibitors of s-adenosylmethionine-dependent methyltransferases.

Montgomery et al (Biol Methylation Drug Design; Proc. Symp. 1985, 409-16) describe as antiviral agents the compound of the above formula wherein $R^a$, $R^b$ and $R^f$ are each hydrogen, $R^c$ and $R^e$ are each hydroxyl and $R^d$ is —CONH$_2$. Two corresponding imidazopyridine derivatives are also described, wherein $R^d$ represents methyl and, chloromethyl respectively.

We have now surprisingly found that certain carbocyclic nucleoside derivatives containing a cyclopentanediol group substituted by a 6-aminopurine or 7-amino-1,2,3-triazolo[4,5-d]pyrimidine group have activity against the parasite *Pneumocystis carinii*, and also against the parasitic protozoa *Trypanosoma brucei gambiense* and *Trypanosoma brucei rhodesiense*.

*Pneumocystis carinii*, is a parasite having a natural habitat in lung tissue. In a host with a normal immune system *P. carinii* is not considered to be pathogenic. However, when the immune system is defective *P. carinii* is liable to cause pneumonia. There is a variety of circumstances in which the immune system may be defective or deficient. Thus, for example immune system deficiency is common in immature or premature infants (neonates). It may also result from suppression by certain drugs, which may be deliberate e.g. in certain patients receiving organ transplants, or unavoidable e.g. as a side-effect of cancer chemotherapy. Disordered growth of one or more constituent parts of the immune system, e.g. as in certain forms of cancer, may also result in immunodeficiency. Immune deficiency may furthermore be caused by viral infections, including human immunodeficiency virus (HIV). It has been reported that at least 60% of patients with acquired immunodeficiency syndrome (AIDS) suffer from *Pneumocystis carinii* pneumonia. In such immunocompromised hosts, prevention of *P. carinii* infection is particularly important.

*Trypanosoma brucei gambiense* and *Trypanosoma brucei rhodesiense* are causative organisms of trypanosomiasis (sleeping sickness).

In one aspect therefore the present invention provides a method of treating or preventing parasitic infections (e.g. infections caused by *Pneumocystis carinii* such as *P. carinii* pneumonia or infections caused by parasitic protozoa such as trypanosamal infections) which comprises administering to a mammal (including a human) in need thereof, a therapeutically effective amount of a compound of general formula (I).

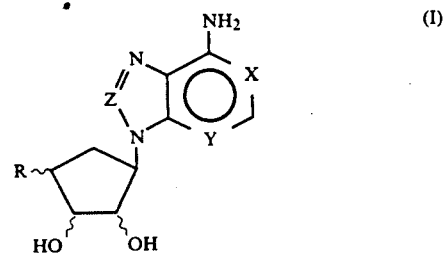

wherein
R represents
a hydrogen atom; a C$_{1-4}$ alkyl group;
a group COR$^1$ wherein R$^1$ represents amino or C$_{1-4}$ alkoxy; or
a group —CH$_2$R$^2$ wherein R$^2$ represents a halogen atom (e.g. chlorine or bromine), C$_{1-4}$ alkylthio, or azido;
X and Y each independently represent —CH— or —N—; and
Z represents —CR$^3$— wherein R$^3$ is hydrogen or C$_{1-4}$ alkyl, or Z represents —N—;
or a physiologically acceptable salt, ester or other physiologically functional derivative thereof.

In another aspect the present invention provides a compound of general formula (I) and physiologically acceptable salts, esters and other physiologically functional derivatives thereof for use in the treatment and/or prophylaxis of parasitic infections in mammals.

In a yet further aspect the present invention provides the use of a compound of formula (I) and physiologically acceptable salts, esters and other physiologically functional derivatives thereof for the manufacture of a medicament for the treatment and/or prophylaxis of parasitic infections in mammals.

In the compounds of formula (I) R is preferably hydrogen or CONH$_2$. Preferably X and Y are both —N— and Z is —CH—, or X, Y and Z each represent —N—.

Examples of physiologically acceptable salts of the compounds according to the invention include acid addition salts formed with organic carboxylic acids such as acetic, lactic, tartaric, maleic, citric, pyruvic, oxalic, fumaric, oxaloacetic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids.

Esters of compounds of formula (I) may be formed at either or both of the 2'- and 3'-hydroxyl groups, e.g. with a carboxylic or sulphonic acid. Alternatively the ester may bridge the 2' and 3'-hydroxyl groups e.g. the 2',3'-sulphite ester. Esters of formula (I) may act as pro-drugs, or may have activity in their own right.

Physiologically functional derivatives of compounds of formula (I) are derivatives which can be converted in the body into the parent compound. Such physiologically functional derivatives may also be referred to as "pro-drugs" or "bioprecursors". Physiologically functional derivatives of compounds (I) include in vivo hydrolysable esters.

It will be appreciated that the compounds of formula (I) may exist in various stereoisomeric forms and the compounds of formula (I) as hereinbefore defined include all stereoisomeric forms and mixtures thereof, including enantiomers and racemic mixtures. The present invention thus includes within its scope the use of any such stereoisomeric form or mixture of stereoisomers, including the individual enantiomers of the compounds of formula (I) as well as wholly or partially racemic mixtures of such enantiomers.

A preferred configuration for the compounds of formula (I) is that represented by formula (IA):

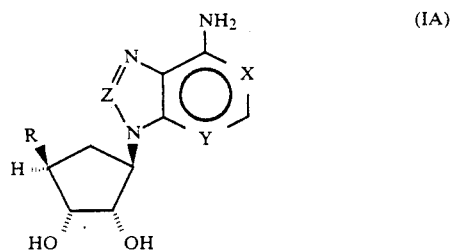

Formula (I) above includes novel compounds as well as certain compounds previously described in the art, albeit for different utilities than are disclosed herein. Thus, in a further aspect the present invention provides a class of novel compounds of formula (I) as hereinbefore defined, and physiologically acceptable salts, esters and other physiologically functional derivatives thereof but with the provisos that:

a) When X and Y are both nitrogen atoms and Z is —CH—, R is not methyl, alkythiomethyl, —CH$_2$Cl or —CONH$_2$;

b) When X is a nitrogen atom and Y and Z both represent —CH—, R is not methyl, —CH$_2$Cl or alkylthiomethyl; and c) When X, Y and Z each represent a nitrogen atom, R is not —CH$_2$Cl.

Preferred novel compounds of formula (I) are those wherein X, Y and Z are as defined above for formula (I) and R is a hydrogen atom. Preferably X and Y are both —N— and Z is —CH—, or X, Y and Z each represent —N—.

Preferred novel compounds according to the present invention include:

(±)-(1R*,2S*,3R*)-3-(6-amino-9H-purin-9-yl)-1,2-cyclopentanediol;

(±)-(1R*,2S*,3S*)-3-(6-amino-9H-purin-9-yl)-1,2-cyclopentanediol; and (±)-(1R*,2S*,3R*)-3-(7-amino-3H-1,2,3-triazolo-(4,5-d)pyrimidin-3-yl)-1,2-cyclopentanediol.

The amount of a compound of formula (I) required for use in the treatment or prophylaxis of parasitic infections will depend inter alia on the route of administration, the age and weight of the patient and the nature and severity of the condition being treated. In general, a suitable dose for administration to man is in the range of 1 to 100 mg. per kilogram bodyweight per day, for example from 10 mg/kg. to 100 mg/kg., per day particularly 10 mg/kg. per day. For administration by inhalation the dose is conveniently in the range of 1 to 50 mg/kg/day, e.g. 5 to 10 mg/kg/day. It will be appreciated that for administration to neonates, lower doses may be required.

For prophylactic treatment the compounds of formula (I) may also be given less frequently, e.g. as a single dose on alternate days, once or twice per week or once or twice per month. The dosage for prophylactic treatment will depend inter alia on the frequency of administration, and, where a depot preparation or controlled release formulation is used the rate of release of the active ingredient. Thus for once-weekly administration a suitable prophylactic dose is in the range 10 to 100 mg/kg, e.g. 5 to 50 mg/kg particularly 15 to 30 mg/kg.

For use according to the present invention the compounds of formula (I) are preferably presented as pharmaceutical formulations. Such pharmaceutical formulations comprise the active ingredient (that is a compound of formula (I) or a physiologically acceptable salt, ester or other physiologically functional derivative thereof) together with one or more pharmaceutically acceptable carriers therefor and optionally other therapeutic and/or prophylactic ingredients. The carrier(s) must be acceptable in the sense of being compatible with the other ingredients of the formulation and not deleterious to the recipient thereof. Pharmaceutical formulations containing a novel compound of formula (I) as herein before defined or a physiologically acceptable salt thereof form a further aspect of the present invention.

The compound of formula (I) or a physiologically acceptable salt, ester or other physiologically functional derivative thereof may conveniently be presented as a pharmaceutical formulation in unit dosage form. A convenient unit dose formulation contains the active ingredient in an amount of from 25 mg to 100 mg.

Pharmaceutical formulations include those suitable for oral, topical (including dermal, buccal and sublingual), rectal or parenteral (including subcutaneous, intradermal, intramuscular and intravenous), nasal and pulmonary administration e.g. by inhalation. The formulation may, where appropriate, be conveniently presented in discrete dosage units and may be prepared by any of the methods well known in the art of pharmacy. All methods include the step of bringing into association the active ingredient with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of the active ingredient. A tablet may be made by compression or moulding, optionally with one or more accessory ingredients. Compressed tablets may be prepared by compressing in a suitable machine the active ingredient in a free-flowing form such as a powder or granules optionally mixed with a binder, lubricant, inert diluent, lubricating agent, surface-active agent or dispersing agent. Moulded tablets may be made by moulding an inert liquid diluent. Tablets may be optionally coated and, if uncoated, may optionally be scored. Capsules may be prepared by filling the active ingredient, either alone or in admixture with one or more accessory ingredients, into the capsule shells and then sealing them in the usual manner. Cachets are analogous to capsules wherein the active ingredient together with any accessory ingredient(s) is sealed in a rice paper envelope. The compounds of formula (I) and physiologically acceptable salts, esters and other physiologically functional derivatives thereof may also be formulated as dispersable granules, which may for example be suspended in water before administration, or sprinkled on food. The granules may be packaged e.g. in a sachet. Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms e.g. tablets wherein the active ingredient is formulated in an appropriate release-controlling matrix, or is coated with a suitable release-controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of the active ingredient with the softened or melted carrier(s) followed by chilling and shaping in moulds.

Pharmaceutical formulations suitable for parenteral administration include sterile solutions or suspensions of the active ingredient in aqueous or oleaginous vehicles. Injectible preparations may be adapted for bolus injection or continuous infusion. Such preparations are conveniently presented in unit dose or multi-dose containers which are sealed after introduction of the formulation until required for use. Alternatively, the active ingredient may be in powder form which is constituted with a suitable vehicle, such as sterile, pyrogen-free water, before use.

The compounds of formula (I) and their physiologically acceptable salts, esters and other physiologically functional derivatives may also be formulated as long-acting depot preparations, which may be administered by intramuscular injection or by implantation e.g. subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing the active ingredient and desirably having a diameter in the range 0.5 to 7 microns are delivered into the bronchial tree of the recipient. Such formulations may be in the form of finely comminuted powders which may conveniently be presented in a pierceable capsule, suitably of, for example, gelatin, for use in an inhalation device, or as a self-propelling formulation comprising active ingredient, a suitable liquid or gaseous propellant and optionally other ingredients such as a surfactant and/or a solid diluent. Suitable surfactants include sorbitan trioleate, Polysorbate 20 and oleic acid. Suitable liquid propellants include propane and the chlorofluorocarbons, and suitable gaseous propellants include carbon dioxide. Self-propelling formulations may also be employed wherein the active ingredient is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microliters, upon each operation thereof.

As a further possibility the active ingredient may be in the form of a solution or suspension for use in an atomiser or nebuliser whereby an accelerated airstream or ultrasonic agitation is employed to produce a fine droplet mist for inhalation. Such solutions or suspensions may comprise in addition to the active ingredient and solvent(s) optional ingredients such as surfactants, for example as described above.

Formulations suitable for nasal administration include presentations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of the active ingredient in aqueous or oily solution or suspension.

It should be understood that in addition to the aforementioned carrier ingredients the pharmaceutical formulations described above may include, as appropriate one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

Therapeutic formulations for veterinary use may conveniently be in either powder or liquid concentrate form. In accordance with standard veterinary formulation practice, conventional water soluble excipients, such as lactose or sucrose, may be incorporated in the powders to improve their physical properties. Thus particularly suitable powders of this invention comprise 50 to 100% w/w, and preferably 60 to 80% w/w of the active ingredient(s), and 0 to 50% w/w and preferably 20 to 40% w/w of conventional veterinary excipients. These powders may either be added to animal feedstuffs, for example by way of an intermediate premix, or diluted in animal drinking water.

Liquid concentrates of this invention suitably contain a water-soluble compound of formula (I) or a salt thereof and may optionally include a veterinarily acceptable water-miscible solvent, for example polyethylene glycol, propylene glycol, glycerol, glycerol formal or such a solvent mixed with up to 30% v/v of ethanol.

The liquid concentrates may be administered to the drinking water of animals.

The compounds of formula (I) may also be used in accordance with the present invention in combination or concurrently with other therapeutic agents, for example agents used in the treatment of immunocompromised patients, e.g. anticancer agents; antiviral agents e.g. azidothymidine (AZT, zidovudine); immunostimulants and immunomodulators.

The present invention also provides a process for the preparation of the compounds of formula (I) which process comprises A) hydroxylation of a compound of formula (II):

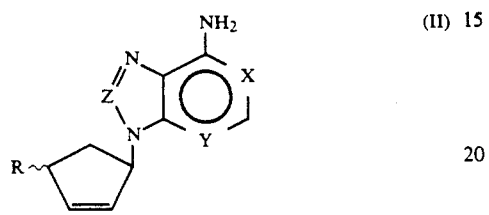

(II)

wherein R, X, Y and Z are as defined for formula (I)

B) to prepare compounds where Z is —CH—, amination of a compound of formula (III):

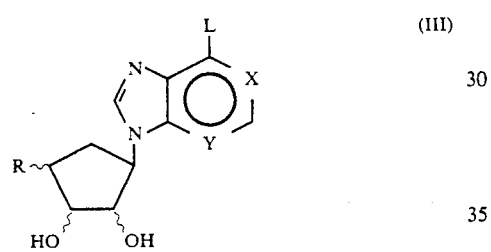

(III)

wherein R, X and Y are as defined for formula (I) and L is a leaving group replaceable by —NH$_2$;

C) to prepare compounds wherein R represents halomethyl, reaction of a compound of formula (IV):

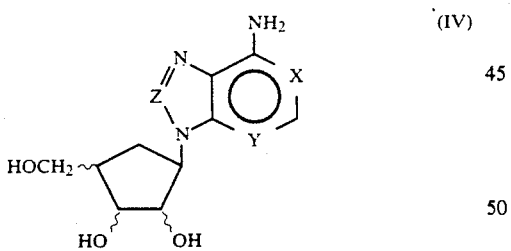

(IV)

wherein X, Y and Z are as defined for formula (I), with a halogenating agent.

D) interconversion of one compound of formula (I) into a different compound of formula (I) e.g. preparation of compounds of formula (I) wherein R represents methyl by reduction of a compound of formula (I) wherein R represents halomethyl, or preparation of compounds (I) wherein R represents —CONH$_2$ by amination of a compound (I) wherein R represents —CO(C$_{1-4}$ alkoxy).

Hydroxylation according to process (A) may be effected using a catalytic amount of osmium tetroxide, in the presence of a tertiary amine oxide, e.g. N-methylmorpholine N-oxide monohydrate. The reaction will generally be carried out in a solvent, preferably an aqueous organic solvent such as an aqueous alcohol e.g. t-butyl alcohol. The reaction temperature may conveniently be between 0° and 150°.

Compounds of formula (II) wherein Z represents —CH— may be prepared by amination of the corresponding compound of formula (V):

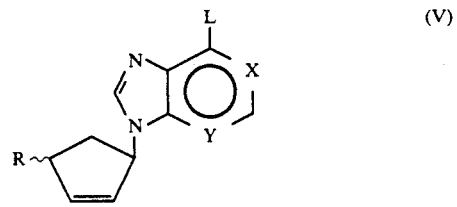

(V)

wherein R, L, X, Y and Z are as hereinbefore defined. The amination may be carried out using ammonia, as described for process (B).

Compounds of formula (V) may themselves be prepared by reaction of a compound of formula (VI):

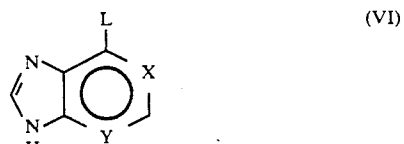

(VI)

with a cyclopentene derivative of formula (VII):

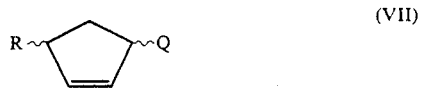

(VII)

(wherein Q is a leaving group e.g. a halogen atom) which may for example be prepared in situ from cyclopentene (or an appropriately substituted derivative thereof) with e.g. N-bromosuccinimide.

Alternatively compounds of formula (V) may be prepared by reaction of a compound of formula (VIII)

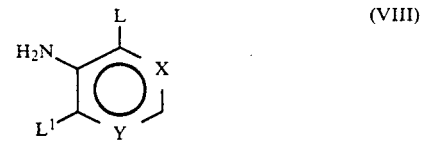

(VIII)

wherein X and Y are as hereinbefore defined and L and L$^1$ each represent leaving groups replaceable by —NH$_2$, with an appropriately substituted 3-aminocyclopentene derivative, in the presence of a solvent, e.g. an alcohol, and a base e.g. triethylamine, at a temperature in the range 50° to 150°, to give a compound of formula (IX):

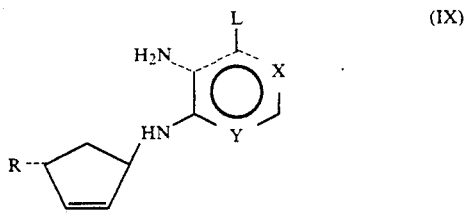

(IX)

followed by cyclisation to a compound of formula (V). The cyclisation may be carried out, e.g., by reacting a compound of formula (IX) with formic acid or a reactive formic acid derivative, e.g. triethylorthoformate or diethoxymethyl acetate, in a solvent such as a dimethylacetamide or acetonitrile at an elevated temperature, preferably at 75°–90°. This reaction is conveniently effected by the addition of a catalytic amount of a strong anhydrous acid, e.g., ethanesulfonic acid in which case lower temperatures, e.g., 25° C., are used. A suitable catalytic amount of the acid may be in the range 0.1 to 2.5%, conveniently around 2%.

Compounds of formula (II) wherein Z is —N— may also be prepared from a compound of formula (IX), by cyclisation in the presence of sodium nitrite and aqueous hydrochloric acid, followed by reaction with ammonium hydroxide. In this reaction, an unstable intermediate corresponding to the 8-aza analogue of formula (V) is believed to be formed in situ.

Amination of a compound of formula (III) according to process (B) may be effected by reaction with ammonia, in the presence or absence of solvent, conveniently at a temperature in the range of 0° to 100° C. Solvents which may be employed in the reaction include water and organic solvents, e.g. alcohols.

A specific embodiment of process (B) comprises aminating a compound of formula (III) wherein R is a group $COR^1$ where $R^1$ represents $C_{1-4}$ alkoxy. In addition to replacement of the leaving group L, the alkoxy group $R^1$ is replaced by $NH_2$, to give a compound of formula (I) wherein R is $-CONH_2$.

Compounds of formula (III) may be prepared by hydroxylation of a compound of formula (V), using the general methods described for process (A) above. Alternatively, compounds of formula (III) may be prepared by cyclisation of a compound of formula (X):

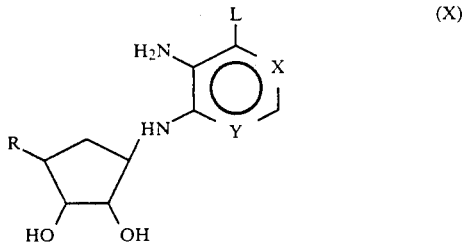

(X)

using similar conditions to those described for the cyclisation of compounds (IX).

Compounds of formula (X) may themselves be prepared by reaction of a compound of formula (VIII) with a compound of formula (XI):

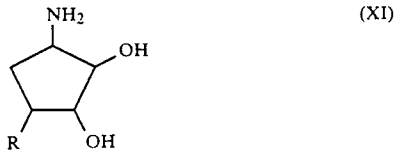

(XI)

wherein R is as hereinbefore defined. Preparation of compounds of formula (XI) may be effected by hydroxylation of a protected 5-(R)-3-amino-cyclopentene derivative, as described for process (A) followed by removal of the protecting group. The amino protecting group may be selected from the conventional protecting groups known in the art. Advantageously the protecting group is a phthaloyl group. Compounds of formula (XI) wherein R is a group $COR^1$ and $R^1$ is $C_{1-4}$ alkoxy may be prepared by the method described by S. Daluge and R. Vince (*J. Org. Chem.* 1978, 12, 2311).

Preparation of compounds of formula (I) according to process (C) may be effected by reaction of a compound of formula (IV) with a halogenating agent, in the presence of a solvent, conveniently at a temperature in the range —15° to +30°. Solvents which may be employed include amides, e.g. hexamethylphosphoramide or N,N-dimethylformamide. The halogenating agent may be for example thionyl chloride, oxalyl chloride or phosphorus pentachloride. Reaction with the halogenating agent will generally be followed by neutralisation, e.g. with ammonium hydroxide. Compounds of formula (IV) may be prepared by the method described in *J. Am. Chem. Soc.* 1969, 91, 3075.

Conversion of a compound of formula (I) wherein R represents halomethyl into a corresponding compound wherein R represents methyl may be effected using a reducing agent such as tributyl tin in the presence of a free radical initiator e.g. α,α-azobisisobutyronitrile. The reaction may conveniently be effected in the presence of an anhydrous solvent e.g. an ether such as tetrahydrofuran.

The invention is further illustrated by the following Examples, which do not however constitute any limitation of the present invention.

EXAMPLE 1 a) (±)-6-Chloro-9-(3-cyclopentenyl)-9H-purine

Cyclopentene (20 g, 0.29 mole), N-bromosuccinimide (26.1 g, 0.147 mole), dibenzoylperoxide (1.0 g, 4.0 mmol) and $CCl_4$ (50 ml) were refluxed for 50 minutes. The resulting mixture was cooled, filtered to remove succinimide, and the filtrate concentrated under reduced pressure (<25° C.) to remove most of the solvent. The residual yellow oil was added dropwise over 30 minutes to a mixture of 6-chloropurine (15.5 g, 0.100 mole) and powdered $K_2CO_3$ (22.9 g, 0.165 mole) in dry DMF (350 ml). The mixture was stirred at ambient temperature overnight. Water (400 ml) and EtOAc (500 ml) were added and the dark EtOAc layer separated. The aqueous layer was extracted with additional EtOAc (2×100 ml) and the combined EtOAc layers dried ($MgSO_4$) and passed through a silica gel pad to remove dark polar material. Evaporation of the EtOAc gave dark yellow syrup (15.4 g). The title compound was eluted with EtOAc from a silica gel column as a yellow oil (8.53 g, 39%). Continued elution gave by-product (±)-6-chloro-7-(3-cyclopentenyl)-9H-purine as pale yellow solid (4.20 g, 19%), mp 124°–126°. Sublimation of a sample of title compound (60°/0.2 mm) gave white crystals, mp 56°–58° C.

Anal. Calcd for $C_{10}H_9ClN_4$: C, 54.43; H, 4.11; Cl, 16.07; N, 25.39. Found: C, 54.43; H, 4.15; Cl, 16.02; N, 25.36.

b) (±) (1R*,2S*,3R*)-3-(6-Chloro-9H-purin-9-yl)-1,2-cyclopentanediol and (±)-(1R*,2S*,3S*)-3-(6-Chloro-9H-purin-9-yl)-1,2-cyclopentanediol (±)-6-Chloro-9(3-cyclopentenyl)-9H-purine (4.41 g, 20.0 mmol) and N-methylmorpholine N-oxide monohydrate (2.84 g, 20.4 mmol as 97%) were dissolved in t-butyl alcohol (125 ml). Osmium tetroxide (0.30 ml of 2.5% solution in t-butyl alcohol) was added and the solution was stirred at 25° for 18 hours. The resulting mixture was evaporated to dryness and the residue chromatographed on silica gel. Elution with MeOH:CHCl$_3$/1:9 gave fractions containing (±)-(1R*,2S*,3S*)-3-(6-chloro-9H-purin-9-yl)-1,2-cyclopentanediol as white crystals (1.92 g), after crystallization from ethanol; mp 154°-156° C.; $^1$H-NMR (Me$_2$SO-d$_6$) δ8.77 (s, 2, purine), 5.05 (d, J=4.9, 2-OH) overlapping 5.1-5.0 (m, 2, H-3), 4.90 (d, J=5.4, 1,1-OH) 4.2-4.1 (m, 1, H-1), 4.05-3.95 (m, 1, H-2), 2.35-2.15 and 1.95-1.75 (both m, 4, two CH$_2$).

Anal. Calcd for C$_{10}$H$_{11}$N$_4$ClO$_2$: C, 47.16; H, 4.35; N, 22.00; Cl, 13.92. Found: C, 47.27; H, 4.35; N, 21.97; Cl, 13.95.

Continued elution of the column gave intermediate fractions containing both title compounds (1.23 g), followed by fractions containing (±)-(1R*,2S*,3R*)-3-(6-chloro-9H-purin-9-yl)-1,2-cyclopentanediol as white crystals (1.08 g), after crystallization from ethanol; mp 153°-157° C.; $^1$H-NMR (Me$_2$SO-d$_6$) δ8.82 and 8.78 (both s, 2, purine), 5.06 (d, J=6.4, 1,2-OH), 4.89 (brq, 1, H-3), 4.78 (d, J=3.2, 1,1-OH), 4.46-4.37 (m, 1, H-2), 4.3-3.9 (m, 1, H-1), 2.35-2.0 and 1.75-1.6 (both m, 4, two CH$_2$).

Anal Calcd for C$_{10}$H$_{11}$N$_4$ClO$_2$: C, 47.16; H, 4.35; N, 22.00; Cl, 13.92. Found: C, 47.22; H, 4.36; N, 21.97; Cl, 13.90.

c) (±)-(1R*,2S*,3R*)-3-(6-Amino-9H-purin-9-yl)-1,2-cyclopentanediol (±)-(1R*,2S*,3R*)-3-(6-Chloro-9H-purin-9-yl)-1,2-cyclopentanediol (4.00 g, 15.7 mmol) and ammonia (1, 100 ml) were stirred in a Parr bomb at 25° C. for 18 hours. Evaporation and neutralization with 1N NaOH (16 ml), followed by elution of a silica gel column with MeOH:CHCl$_3$/1:4 gave title compound as white crystals, recrystallized from 95% ethanol (3.54 g, 96%); mp 201°-202° C.; $^1$H-NMR (Me$_2$SO-d$_6$) δ8.19 and 8.12 (both s, 2, purine H-2, H-8), 7.18 (br s, 2, NH$_2$), 4.98 (d, J=6.6, 1, 2-OH), 4.76-4.64 (m) overlapping 4.70 (d, J=3.4, 2, H-3 and 1-OH), 4.42-4.34 (m, 1, H-2), 4.04-3.97 (m, 1, H-1), 2.5-1.9 and 1.7-1.6 (both m, 4, two CH$_2$).

Anal. Calcd for C$_{10}$H$_{13}$N$_5$O$_2$: C, 51.06; H, 5.57; N, 29.77. Found: C, 50.98; H, 5.58; N, 29.72.

EXAMPLE 2

(±)-(1R*,2S*,3S*)-3-(6-Amino-9H-purin-9-yl)-1,2-cyclopentanediol (±)-(1R*,2S*,3S*)-3-(6-Chloro-9H-purin-9-yl)-1,2-cyclopentanediol (0.509 g, 2.00 mmol) was aminated as in Example 1(c) to give the title compound as white powder (0.210 g, 45%), after elution from a silica gel coloumn with MeOH:CHCl$_3$/1:4; mp >250° C.; $^1$H-NMR (Me$_2$SO-d$_6$) δ8.21 and 8.12 (both s, 2, purine H-2 and H-8), 7.16 (br s, 2, NH$_2$), 4.97 (d, J=4.6, 1,2-OH), 4.87 (d, J=5.9) overlapping 4.91-4.80 (m, 2,1-OH and H-3), 4.18-4.08 (m, 1, H-1), 3.98-3.90 (m, 1, H-2), 2.3-2.05 and 1.95-1.68 (both m, 4, two CH$_2$).

Anal. Calcd for C$_{10}$H$_{13}$N$_5$O$_2$: C, 51.06; H, 5.57; N, 29.77. Found: C, 51.15; H, 5.63; N, 29.75.

EXAMPLE 3 a) (±)-5-Amino-4-chloro-6[(2-cyclopent-1-yl)amino]pyrimidine

3-Aminocyclopentene (R. Vince and S. Daluge, *J. Med. Chem.* 1974, 17, 578) (6.58 g, 79 mmol), 5-amino-4,6-dichloropyrimidine (13.40 g, 81.9 mmol), triethylamine (16.5 g, 164 mmol) and 1-butanol (125 ml) were refluxed under nitrogen for 18 hours and then evaporated to tan solid which was recrystallized from methanol to give the title compound as off-white crystals (12.67 g, 76%); mp 169°-173° C.; $^1$H-NMR (Me$_2$SO-d$_6$) δ7.72 (s, 1, pyrimidine H-2), 6.75 (br d, J=6.9, 1, NH), 6.05-5.90 and 5.85-5.70 (both m, 2, CH=CH), 5.07 (br s, 3, NH$_2$ and CH-N), 2.4-2.2 and 1.7-1.5 (both m, 4, two CH$_2$).

Anal. Calcd. for C$_{10}$H$_9$ClN$_4$: C, 54.43; H, 4.11; N, 25.39; Cl, 16.07. Found: C, 54.43; H, 4.15; N, 25.36; Cl, 16.02.

b) (±)-7-Amino-3-(2-cyclopenten-1-yl)-1,2,3-triazolo[4,5-d]pyrimidine (±)-5-Amino-4-chloro-6[(2-cyclopent-1-yl)amino]pyrimidine (5.62 g, 26.7 mmol) was dissolved in 1N HCl (53 ml) and H$_2$O (50 ml). This chilled solution (ice bath) was stirred while a solution of sodium nitrite (2.20 g, 32.0 mequiv) in H$_2$O (10 ml) was added over 1 minute. The resulting cloudy mixture was stirred vigorously in the ice bath for 5 minutes. The bath was removed and concentrated ammonium hydroxide (100 ml) was added. The mixture was heated to 70° C. over 10 minutes, then allowed to come to room temperature. The cooled mixture was filtered to give title compound as white powder, after washing with water and drying under vacuum (4.80 g, 89%); mp 207°-208° C.; $^1$H-NMR (Me$_2$SO-d$_6$) δ8.40 and 8.05 (br s) overlapping 8.27 (s) (total 3, tautomers NH$_2$ and H-5), 6.23-6.19 (m, 1, =CH), 5.95-5.80 (m, 2, =CH and CH-N), 2.9-2.1 (m overlapping solvent, two CH$_2$).

Anal. Calcd. for C$_9$H$_{10}$N$_6$: C, 53.45; H, 4.98; N, 41.56. Found: C, 53.42; H, 4.98; N, 41.51.

c) (±)-(1R*,2S*,3R*)-3-(7-Amino-3H-1,2,3-triazolo[4,5-d]pyrimidin-3-yl)-1,2-cyclopentanediol (±)-7-Amino-3-(2-cyclopenten-1-yl)-1,2,3-triazolo[4,5-d]pyrimidine (4.80 g, 23.7 mmol), N-methylmorpholine N-oxide monohydrate (3.15 g, 26.1 mmol as 97%), water (35 ml), t-butylalcohol (175 ml) and 2.5% osmium tetroxide in t-butyl alcohol (1.0 ml) were refluxed for 3 hours and then stirred at 25° C. for 18 hours. The resulting mixture was evaporated to dryness and chromatographed on silica gel. Title compound was eluted with MeOH:CHCl$_3$/1:3 to give white crystals after two recrystallizations from ethanol-water (3.74 g, 67%); mp 244°-245° C.; $^1$H-NMR (Me$_2$SO-d$_6$) δ8.26 (s, 1, H-5'), 8.35 and 8.05 (both br s) overlapping 8.26 (s) (total 3 protons, tautomers NH$_2$ and H-5'), 5.2-5.0 (m) overlapping 5.01 (d, J=7.3) (total 2, OH and H-3), 4.72 (d, J=3.5, 1, OH), 4.5-4.4 (m, 1, H-2), 4.1-4.0 (m, 1, H-1), 2.4-1.6 (m, 4, two CH$_2$).

Anal. Calcd. for C$_9$H$_{12}$N$_6$O$_2$: C, 45.76; H, 5.12; N, 35.58. Found: C, 45.50; H, 5.18; N, 35.45.

EXAMPLE 4

(±)-(1R*,2S*,3R*,5S*)-3-(6-Amino-9H-purin-9-yl)-5-(chloromethyl)-1,2-cyclopentanediol (±)-(1R*,2S*,3R*,5R*)-3-(6-Amino-9H-purin-9-yl)-5-(hydroxymethyl)-1,2-cyclopentanediol (*J. Am. Chem. Soc.* 1969, 91, 3075) (0.94 g, 3.54 mmol) was stirred in hexamethylphosphoramide (13 ml) with cooling (ice bath) while thionyl chloride was added. The mixture was stirred under nitrogen at 25° C. for 18 hours. Ice water (50 ml) was added to the cooled mixture. The resulting solution was neutralized with concentrated ammonium hydroxide. The white precipitate was filtered off and dissolved in refluxing methanol (125 ml). Concentrated ammonium hydroxide (10 ml) was added and the solution allowed to cool slowly to 25° C. over 1 hour. The methanol was evaporated and the residual solid slurried in cold water and filtered to give title compound as an off-white powder (0.92 g, 92%); mp 188°–189° C. dec.

Anal. Calcd. for $C_{11}H_{14}ClN_5O_2 \cdot w\ H_2O$: C, 45.84; H, 5.07; N, 24.30; Cl, 12.30. Found: C, 45.81; H, 5.05; N, 24.33; Cl, 12.22.

EXAMPLE 5

(±)-(1R*,2S*,3R*,5S*)-3-(6-Amino-9H-purin-9-yl)-5-methyl-1,2-cyclopentanediol (±)-(1R*,2S*,3R*,5S*)-3-(6-Amino-9H-purin-9-yl)-5-(chloromethyl)-1,2-cyclopentanediol (568 mg, 1.97 mmol) was refluxed in dry tetrahydrofuran (65 ml) with tributyltin hydride (2.27 ml) and α,α'-azobisisobutyronitrile (194 mg) for 5 days. Solvent was evaporated and the residual syrup triturated with hexanes (50 ml). The resulting gray powder was filtered, washed with hexanes and chromatographed on silica gel. Title compound was eluted with MeOH:CHCl₃/1:4 as white solid foam (0.50 g) which crystallized from ethanol-water (424 mg, 86%); mp 208°–211° C.; ¹H-NMR (Me₂SO-d₆) δ8.18 and 8.10 (both s, 2, purine H-2,8), 7.15 (br s, 2, NH₂), 4.88 (d, J=6.1, 1, OH). 4.68 (d, J=4.8) overlapping 4.75–4.50 (m, total 2, OH and H-3), 4.40–4.25 (m, 1, H-2), 3.70–3.55 (m, 1, H-1), 2.35–2.15 (m, 1, H-5), 2.0–1.8 and 1.7–1.5 (both m, 2, CH₂), 1.10 (d, J=6.9, 3, CH₃).

Anal. Calcd. for $C_{11}H_{15}N_5O_2 \cdot 3/10\ H_2O$: C, 51.88; H, 6.17; N, 27.50. Found: C, 51.92; H, 6.20; N, 27.49.

EXAMPLE 6

(±)-(1R*,2S*,3R*,4S*)-4-(6-Amino-9H-purin-9-yl)-2,3-dihydroxy-1-cyclopentanecarboxamide (±)-(1α,2β,3β,4α)-Methyl 4-acetamido-2,3-diacetoxy-1-cyclopentane carboxylate (R. C. Cermak and R. Vince, *Tetrahedron Letters* 1981, 22, 2331) (6.02 g, 20.0 mmol) and 2 hydrochloric acid (120 ml) were refluxed for 4 hours. The solution was evaporated to a syrup. Water was removed by distillation of n-butanol (250 ml). The residue was dissolved in n-butanol (100 ml) and triethylamine (14 ml, 0.100 mole) and 5-amino-4,6-dichloropyrimidine (6.56 g, 40.0 mmol) added. After 18 hours of reflux, volatiles were evaporated and the residual syrup partitioned between methylenechloride (250 ml) and saturated aqueous sodium bicarbonate (50 ml). The methylene chloride layer was dried (MgSO₄) and the contents chromatographed on a silica gel flash column. Elution with 2–4% methanol-chloroform gave the butyl ester of the pyrimidine intermediate as white solid (4.49 g); crystallisation of such a sample from chloroform gave white crystals, mp 126°–128°. The pyrimidine intermediate (4.49 g, 13.4 mmol) was stirred with triethylorthoformate (12 ml) and ethanesulphonic acid (40 mg) at 35° for 18 hours. The residual syrup remaining after evaporation of most of the triethylorthoformate was dissolved in 1N HCl (25 ml) and dioxane (25 ml). After 30 minutes the solution was neutralized with sodium bicarbonate and extracted with chloroform (50 ml). The chloroform layer was dried (MgSO₄) and evaporated to a yellow syrup (5.0 g) which was chromatographed on silica gel. Elution with ethylacetate gave (±)-(1R*,2S*,3S*,4S*)-butyl-4-(6-chloro-9H-purin-9-yl)-2,3-dihydroxy-1-cyclopentanecarboxylate as white solid (3.42 g, 72%); mp 104°–106°; structure confirmed by ¹H-NMR and mass spectrum. Amination of such a sample of 6-chloropurine derivative (1.00 g, 2.82 mmol) in a Parr bomb with liquid ammonia (100 ml) at 25° for 18 hours gave a mixture which was chromatographed on silica gel. Elution with 10% methanol-chloroform gave (±)-(1R*,2S*,3R*,4S*)-butyl-4-(6-amino-9H-purin-9-yl)-2,3-dihydroxy-1-cyclopentanecarboxylate as white solid (0.37 g); mp 173°–175°, after crystallisation from acetonitrile; structure confirmed by ¹H-NMR and mass spectrum. Continued elution gave fractions containing the 1'-epimer, (±)-(1R*,2R*,3S*,4S*,-butyl-4-(6-amino-9H-purin-9-yl)-2,3-dihydroxy-1-cyclopentanecarboxylate (0.35 g) as white crystals (from acetonitrile); mp 214°–216° C.; structure confirmed by ¹H-NMR and mass spectrum.

Continued elution with 40–80% methanol-chloroform gave title compound as white powder (0.27 g). Recrystallisation of such a sample from 95% ethanol gave white crystals; mp 185°–191°; ¹H-NMR (Me₂SO-d₆) δ8.24 and 8.10 (both s, 2, purine H-2 and H-8), 7.68 (brd, 2, CONH₂), 7.17 (brs, 2, NH₂), 5.065 (d, J=6.1, 1, OH), 4.94 (d, J=4.9, 1, OH), 4.69, 4.28 and 4.08 (all m, 3, 2 CH-0 and 1 CH-N), 2.72 (m, 1, CHCONH₂), 2.4–2.0 (m, 2, CH₂). Anal Calcd for $C_{11}H_{14}N_6O_3 \cdot 2.1\ H_2O$: C, 41.80; H, 5.80; N, 26.59. Found: C, 41.39; H, 5.30; N, 26.14.

Continued elution of the column gave the 1'-epimer of title compound, (±)-(1R*,2R*,3S*,4R*)-4-(6-amino-9H-purin-9-yl)-2,3-dihydroxy-1-cyclopentanecarboxamide, as white solid (0.10 g). Crystallisation of such a sample from ethanol-water gave white crystals, mp 258°–261° dec; structure confirmed by ¹H-NMR and mass spectrum. Anal. Calcd for $C_{11}H_{14}N_6O_3 \cdot \frac{1}{4}\ H_2O$: C, 46.72; H, 5.17; N, 29.72. Found: C, 46.82; H, 5.17; N, 29.68.

In another experiment in which the ethyl ester of the 6-chloropurine intermediate was subjected to the same amination conditions, the yield of title compound was greater (67%), after column separation from the lower R_f epimer.

EXAMPLE 7

(±)-(1R,2S,3R)-3-(6-Amino-8-methyl-9H-purin-9-yl)-1,2-cyclopentanediol

A solution of (±)-(1R,2S,3R)-3-[(5-amino-6-chloro-4-pyrimidinyl)amino]-1,2-cyclopentanediol (1.00 g, 4.09 mmol) in trimethyl orthoacetate (20 ml) and ethane sulfonic acid (1 drop) was heated at 130° for two hours. Solvent was evaporated and residual oil stirred in NaOH (1N, 30 ml) and dioxane (10 ml) under nitrogen for 2.5 hours at room temperature. Concentrated HCl was added to bring to pH 1.0 and the resulting solution was stirred for two hours. NaOH (5N) was added to bring the mixture to pH10 for 10 minutes and the solution was neutralized and evaporated to dryness. Elution from a silica gel column with 10% methanol-ethyl acetate gave fractions containing the 6-chloro analogue of title compound. Such a sample (300 mg) was heated at 60° C. in liquid ammonia (50 ml) for 12 hours in a Parr bomb. The ammonia was evaporated and the residual solid chromatographed on silica gel. Elution with 8% methanol-chloroform gave (±)-(1R,2S,3R)-3-(6-methoxy-8-methyl-9H-purin-9-yl)-1,2-cyclopentanediol (100 mg). Continued elution with 18% methanol-chloroform gave the title compound as a white powder after crystallisation from ethanol (0.398 g) m.p. 271°–274°; ¹H-NMR (DMSO-d₆) δ: 8.05 (s, 1 purine H-2), 7.0 (6, s, 2, NH₂) 4.90 (m, 1, OH). 4.70 (m, 1, OH), 4.60–4.50 (m, 2, 2 CH-OH), (4.0 m, 1, CH-N), 2.55 (s, overlapping solvent, CH₃) 2.40–2.10 (m, 3, 3/2 CH₂), 1.75–1.60 (m, 1, ½ CH$_2$). Anal calculated for C$_{11}$H$_{15}$N$_5$O$_2$C, 53.01; H, 6.07; N, 28.10. Found, C, 53.06, H, 6.08; N, 28.12.

BIOLOGICAL TEST RESULTS

A) Activity against Trypanosoma brucei gambiense
Method
1. *T. brucei* subsp. gambiense procyclic (strain TH114 from the Institut fur Schiffs und Tropenkrankheiten, Hamburg) were grown in medium PDM-79 (Fish et al; BBA714[1982]422–428) in 25 cm$^2$ tissue (T-25) culture flasks at 27° C. in a 5% CO$^2$/air atmosphere. Drugs were dissolved in 0.1N NaOH and their concentration determined from their spectral data.

Drugs were added to the PDM-79 at a volume ≦1% of the total volume and the drug containing medium filter-sterilised into T-25 flasks. Flasks were inoculated to a final density of ≃10$^5$/ml and incubated for 5 days at which time their density was determined by a Coulter Counter (Model ZB1). Results were expressed as % inhibition relative to the controls.

Results

| Compound of Example: | I$_{50}$ (μM) |
|---|---|
| 1C | 0.0007 |
| 2 | 1.0 |
| 3C | 0.20 |
| 4 | 3.5 |
| 5 | 0.002 |
| 6 | 0.04–0.2 |

(B) Activity against *Pneumocystis carinii*
Method
The compounds were tested according to the method of Pesanti, (*J. Infect. Dis.*, 141(6), 775–780, 1980).
Results

| Compound of Example: | I$_{50}$ (μM) |
|---|---|
| 2 | <20 |
| 3C | <20 |

TOXICOLOGY TEST

Charles River CD rats were given oral doses of the compound of Example 3 at 4 mg/kg for 30 days. No treatment-related changes were observed with respect to clinical signs of toxicity, body weight, clinical pathology or pathology.

The following examples illustrate pharmaceutical formulations which may be employed in accordance with the present invention;

Injectable solution
A solution for intramuscular injection may be prepared by mixing:

| | |
|---|---|
| Compound of formula (I) | .9.5 parts by weight |
| Dimethyl sulphoxide | 19.0 parts by weight |
| Sorbitan monooleate | 4.5 parts by weight |
| Corn oil | 67.0 parts by weight |
| | 100.0 |

Injectable solution

| | |
|---|---|
| Compound of formula (I) | 5 parts by weight |
| N-methyl-pyrollidone | 48.3 parts by weight |
| Tween 80 | 2 parts by weight |
| Span 80 | 4.7 parts by weight |
| Miglyol 812 | 40 parts by weight |
| | 100.0 |

Tablet

| | |
|---|---|
| Compound of formula (I) | 25.0 mg |
| Lactose BP | 48.5 mg |
| Microcrystalline Cellulose BP ("Avicel pH 101") | 10.0 mg |
| Low-substituted Hydroxypropyl; Cellulose BP ("LHPC LH-11") | 10.0 mg |
| Sodium Starch Glycollate BP ("Explotab") | 3.0 mg |
| Povidone BP ("K30") | 3.0 mg |
| Magnesium Stearate BP | 0.5 mg |
| | 100.0 mg |

Oral suspension

| | |
|---|---|
| Compound of formula (I) | 50 mg |
| Avicel RC 591 | 75 mg |
| Sucrose syrup | 3.5 ml |
| Methylhydroxybenzoate | 5 mg |
| Colour | 0.01% w/v |
| Cherry flavour | 0.1% v/v |
| Tween 80 | 0.2% v/v |
| Water | to 5 ml |

Injectable suspension

| | |
|---|---|
| Compound of formula (I) | 100 mg |
| Polyvinyl pyrrolidone (PVP) | 170 mg |
| Tween 80 | 0.2% v/v |
| Methylhydroxybenzoate | 0.1% w/v |
| Water for Injection | to 3 ml |

Capsule

| | |
|---|---|
| Compound of formula (I) | 100 mg |
| Starch 1500 | 150 mg |
| Magnesium stearate | 2.5 mg |
| filled into a hard gelatin capsule | |

Suspension for Nebulisation

| | |
|---|---|
| Compound of formula (I), sterile | 1.0 mg |
| Water for Injections | to 10.0 ml |

Disperse the compound of formula (I) in the Water for Injections previously sterilised in a sterile container. Fill in to sterile glass ampoules, 10 ml/ampoule under aseptic conditions, and seal each ampoule by fusion of the glass.

Aerosol Formulation

| | |
|---|---|
| Compound of formula (I), micronised | 1.0 mg |
| Aerosol propellant | to 5.0 ml |

Suspend the micronised compound of formula (I) in the aerosol propellant. Fill this suspension into preformed aerosol cannisters, 5 ml/cannister under pressure, through the valve orifice.

Powder Inhalation

| | |
|---|---|
| Compound of formula (I), micronised | 1.0 mg |
| Lactose | 29.0 mg |

Triturate and blend the micronised compound of formula (I) with the lactose. Fill the resulting powder blend into hard gelatin capsule shells, 30 mg per capsule.

Nasal Drops

| | |
|---|---|
| Compound of formula (I) | 100.0 mg |
| Methylhydroxybenzoate | 10.0 mg |
| Water for Injections | to 10.0 ml |

Disperse the compound of formula (I) and the methylhydroxybenzoate in the Water for Injections. Fill this suspension into suitable dropper bottles, 10 ml/bottle, and close by securing the dropper nozzle and bottle cap.

I claim:

1. A method for the treatment of an infection caused by *Pneumocystis carinii*, trypanosomal bruce: gambiense or trypanosoma bruce; rhodesiense in a mammal which comprises administering to said infected mammal a therapeutically effective infection treatment amount of a compound of formula (I)

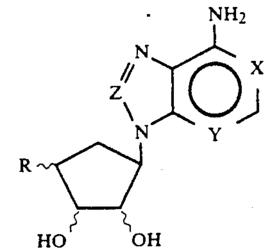

(I)

wherein R represents hydrogen; $C_{1-4}$ alkyl; $COR^1$ wherein $R^1$ represents amino or $C_{1-4}$ alkoxy; or $—CH_2R^2$ wherein $R^2$ represents halogen; $C_{1-4}$ alkylthio or azido;

X and Y each independently represent —CH—; and

Z represents —N—;

or a physiologically acceptable salt, an ester formed from a carbocyclic or sulphonic acid or other physiologically functional derivative thereof.

2. A method according to claim 1 wherein in the compound of formula (I) R is hydrogen or $—CONH_2$.

3. A method according to claim 1 wherein the compound of formula (I) has the configuration (IA)

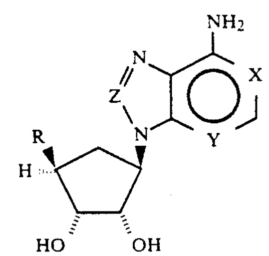

(IA)

wherein R, X, Y and Z are as defined in claim 1.

4. A method according to claim 1 wherein the parasitic infection is due to *Pneumocystis carinii*.

5. A method according to claim 1 wherein the parasitic infection is a trypanosomal infection.

6. A method according to claim 4 or claim 5 wherein the mammal is a human.

7. A compound of formula (I) wherein X, Y and Z are as defined in claim 1 and R is hydrogen.

8. A pharmaceutical formulation comprising a compound of formula (I) as defined in claim 7, or a physiologically acceptable salt, ester or other physiologically functional derivative thereof together with a pharmaceutically acceptable carrier therefor.

* * * * *